April 27, 1954 O. E. McGUIRE Plant Pat. 1,272
PEPEROMIA PLANT
Filed Nov. 4, 1952
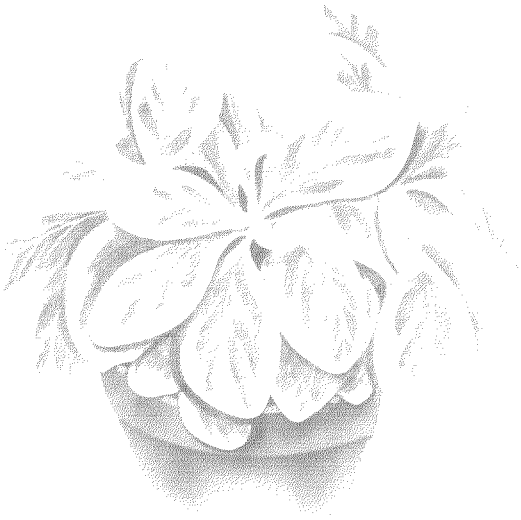
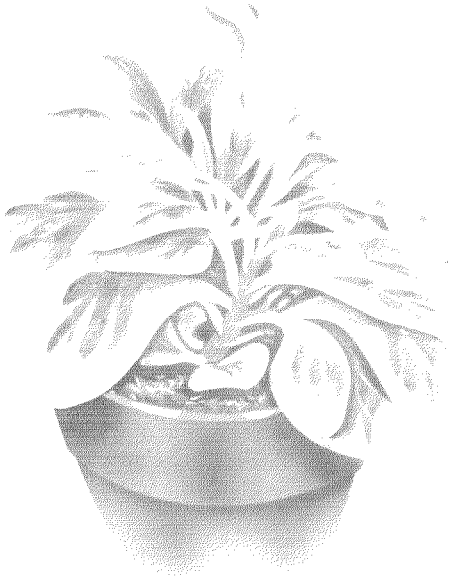
INVENTOR
O. E. McGUIRE
BY A. Yates Dowell
ATTORNEY Patented Apr. 27, 1954

Plant Pat. 1,272

UNITED STATES PATENT OFFICE 1,272

PEPEROMIA PLANT

Orvid E. McGuire, Apopka, Fla., assignor to The Evergreen Gardens, Apopka, Fla.

Application November 4, 1952, Serial No. 318,771

1 Claim. (Cl. 47—59)

The present invention relates to a new and distinct variety of peperomia plant which originated as a sport of the variety *Peperomia obtusifolia variegata.*

The new variety was discovered by me in my greenhouse as a sport on the parent plant. It has been asexually reproduced through nine generations, its characteristics holding true throughout all the more than six thousand specimens produced. The plant has been asexually reproduced in my greenhouse in Apopka, Florida, by tip cuttings and also by taking a section of the stem with a leaf and eye.

The upper representation on the drawing is a top view of a six months old specimen of the plant, taken at a slight angle, which illustrates the shape and pattern of the leaves and the compactness of the plant.

The lower is a side view which illustrates the arrangement of the leaves on the stem and the self-branching characteristic of the plant.

The plant is easily distinguished from its parent in that the new variety is a dwarf, very compact in growth, and freely self-branching. It has a slightly greater rate of growth than its parent, and will reach a height of two or three inches in approximately six months. The plant grows in a spreading up-right position with a circumference spread of approximately six to twelve inches. The leaves grow more closely together on the stem and are far more numerous than those of the parent. The leaf count ranges from approximately twenty-five to forty-five, depending on the height and number of the branches. Branching may occur from any of the eyes in the stem, an eye being located immediately above each petiole. The leaves generally sprout from alternate sides of the stem as the plant grows, the petiole curving slightly from the stem at approximately a 45° angle. The leaves vary in size from approximately one-half to one and one-half inches in width and from one to two inches in length. They are obtusely obovate and have a grey-green to green center area with lighter veins and nerves running to the oyster-white irregular border of variable width of the leaf. The leaves appear translucent, the typical pattern being visible, although somewhat less distinct, on the underside of the leaf. The central green area is generally a trifle darker than "Lettuce Green" Plate No. 74, and a trifle lighter than "Spinach Green" Plate No. 75, Koster's Color Guide, copyright 1931, although the shade of green may vary slightly under different conditions of growth. The main stem of the plant is a lighter shade of green than the green portions of the leaves and has an occasional blotch of red mingled in.

The resistance of the plant to low temperatures is good, the plant being able to withstand a temperature of 33° F. for several hours.

In contrast to the maximum height of five to six inches which it is believed the new variety can attain in approximately twelve to eighteen months, the parent usually reaches a height of twelve to eighteen inches when full grown. The leaves of the parent are approximately three to five times as large as those of the new variety. The central green portion of the leaves is generally slightly darker than that of the new variety. In addition, the parent does not usually branch unless a tip is cut from the main stem.

Having thus disclosed my discovery, I claim:

The new and distinct peperomia plant disclosed, characterized by its similarity in its leaf pattern to its parent *Peperomia obtusifolia variegata,* but differing therefrom by its dwarf, compact and self-branching habit of growth, and its greatly more abundant and smaller leaves.

No references cited.